US010035831B2

(12) United States Patent
Kanai et al.

(10) Patent No.: US 10,035,831 B2
(45) Date of Patent: Jul. 31, 2018

(54) OXIDIZED Aβ PEPTIDE

(71) Applicant: JAPAN SCIENCE AND TECHNOLOGY AGENCY, Kawaguchi-shi (JP)

(72) Inventors: Motomu Kanai, Bunkyo-ku (JP); Yohei Soma, Bunkyo-ku (JP); Atsuhiko Taniguchi, Yokohama (JP); Daisuke Sasaki, Sumida-ku (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 14/898,409

(22) PCT Filed: Jun. 13, 2014

(86) PCT No.: PCT/JP2014/065749
§ 371 (c)(1),
(2) Date: Dec. 14, 2015

(87) PCT Pub. No.: WO2014/200091
PCT Pub. Date: Dec. 18, 2014

(65) Prior Publication Data
US 2016/0137706 A1 May 19, 2016

(30) Foreign Application Priority Data

Jun. 14, 2013 (JP) ................. 2013-125797
Nov. 20, 2013 (JP) ................. 2013-239622

(51) Int. Cl.
*C07K 14/47* (2006.01)
*C07K 1/113* (2006.01)
*A61K 38/00* (2006.01)

(52) U.S. Cl.
CPC .......... *C07K 14/4711* (2013.01); *C07K 1/113* (2013.01); *A61K 38/00* (2013.01)

(58) Field of Classification Search
CPC ..... A61K 38/00; C07K 1/113; C07K 14/4711
See application file for complete search history.

(56) References Cited

U.S. PATENT DOCUMENTS

| 6,787,523 B1 * | 9/2004 | Schenk | A61K 38/1709 424/1.57 |
| 2008/0131422 A1 | 6/2008 | Sugimura et al. | |
| 2010/0267816 A1 | 10/2010 | Sugimura et al. | |
| 2011/0286932 A1 | 11/2011 | Koronyo et al. | |

FOREIGN PATENT DOCUMENTS

| AU | 2003227475 | 11/2003 |
| CA | 2017987 | 12/1990 |
| EP | 1 741 783 A1 | 1/2007 |
| FR | 2879403 | 6/2006 |
| JP | 03-020220 | 1/1991 |
| JP | 2012-503012 A | 2/2012 |
| WO | 03/084545 | 10/2003 |

OTHER PUBLICATIONS

Extended European Search Report dated Dec. 16, 2016 in Patent Application No. 14810613.1.
Christian Schöneich, et al., "Cu(II)—Catalyzed Oxidation of β—Amyloid Peptide Targets His[13] and His[14] over His[6]: Detection of 2-Oxo-histidine by HPLC-MS/MS," Chem. Res. Toxicol. vol. 15, No. 5 (2002), pp. 717-722.
D.H. Lopes, et al., "Induction of methionine-sulfoxide reductase protects neurons from amyloid β-protein insults in vitro and in vivo," Abstracts of the Annual Meeting of the Society for Neuroscience, Society for Neuroscience, vol. 41, (2011), 2 pages.
C. Behl, et al., "Hydrogen Peroxide Mediates Amyloid β Protein Toxicity," Cell, vol. 77, Jun. 17, 1994, pp. 817-827.
D. Allan Butterfield, et al., "The critical role of methionine 35 in Alzheimer's amyloid β-peptide (1-42)—induced oxidative stress and neurotoxicity," Biochimica et Biophysica Acta, vol. 1703, No. 2, (2005), pp. 149-156.
Danielle G. Smith, et al., "The redox chemistry of the Alzheimer's disease amyloid β peptide," Biochimica et Biophysica Acta, vol. 1768, No. 8, (2007), pp. 1976-1990.
Christian Schoneich, "Selective $Cu^{2+}$/Ascorbate-Dependent Oxidation of Alzheimer's Disease β-Amyloid Peptides", Annals New York Academy of Science, vol. 1012, pp. 164-170, (2004).
Koichi Inoue, et al., "Liquid chromatography/tandem mass spectrometry characterization of oxidized amyloid beta peptides as potential biomarkers of Alzheimer's disease", Rapid Communications in Mass Spectrometry, vol. 20, pp. 911-918, (2006).
Sergio Giunta, et al., "Transformation of beta-amyloid (Aβ) (1-42) tyrosine to L-Dopa as the result of in vitro hydroxyl radical attack", Amyloid: Int. J. Exp. Clin. Invest., vol. 7, pp. 189-193, (2000).
Atsuhiko Taniguchi, et al., "Attenuation of the Aggregation and Neurotoxicity of Amyloid-β Peptides by Catalytic Photooxygenation", Angewandte Chemie International Edition, vol. 53, pp. 1382-1385, (Jan. 27, 2014).
John Hardy, et al., "The Amyloid Hypothesis of Alzheimer's Disease: Progress and Problems on the Road to Therapeutics", Science, vol. 297, pp. 353-356, (Jul. 19, 2002).
Stephen A. Gravina, et al., "Amyloid β Protein (Aβ) in Alzheimer's Disease Brain", The Journal of Biological Chemistry, vol. 270, No. 13, Issue of Mar. 31, pp. 7013-7016, (1995).
Liming Hou, et al., "Methionine 35 Oxidation Reduces Fibril Assembly of the Amyloid Aβ(1-42) Peptide of Alzheimer's Disease", The Journal of Biological Chemistry, vol. 277, No. 43, Issue of Oct. 25, pp. 40173-40176, (2002).

(Continued)

*Primary Examiner* — Gregory S Emch
(74) *Attorney, Agent, or Firm* — Oblon, McClelland, Maier & Neustadt, L.L.P.

(57) ABSTRACT

The invention provides an Aβ peptide aggregation inhibitor, an Aβ peptide toxicity reducing agent, and a preventive and/or therapeutic agent for Alzheimer's disease. The oxidized Aβ peptide in which one or more amino acid residues of Aβ peptide have been oxidized (excluding an oxidized Aβ peptide in which only Met has been oxidized).

8 Claims, 13 Drawing Sheets

(56) References Cited

OTHER PUBLICATIONS

Gal Bitan, et al, "A Molecular Switch in Amyloid Assembly: Met[35] and Amyloid β-Protein Oligomerization", J. Am. Chem. Soc., vol. 125, No. 50, pp. 15359-15365, (2003).
Jackob Moskovitz, et al., "Induction of Methionine-Sulfoxide Reductases Protects Neurons from Amyloid β-Protein Insults in Vitro and in Vivo", Biochemistry, vol. 50, pp. 10687-10697, (2011).
International Search Report dated Sep. 9, 2014 in PCT/JP14/065749 Filed Jun. 13, 2014.
Office Action as received in the corresponding European Patent Application No. 14810613.1-1111 dated Jan. 12, 2018, citing documents AX and AY therein, 7 pages.
Jerzy W. Naskalski, et al., "Oxidative Modifications of Protein Structures", Advances in Clinical Chemistry, vol. 35, 2001, pp. 161-253.
Grzegorz Bartosz, "Chemical Biological and Functional Properties Chapter 8", Food Oxidants and Antioxidants: Chemical, Biological, and Functional Properties, Jan. 1, 2013, p. 197-225.
Office Action as received in the corresponding Japanese Patent Application No. 2013-239622 dated Sep. 19, 2017 w/Partial English Translation.

\* cited by examiner

[Fig. 1]
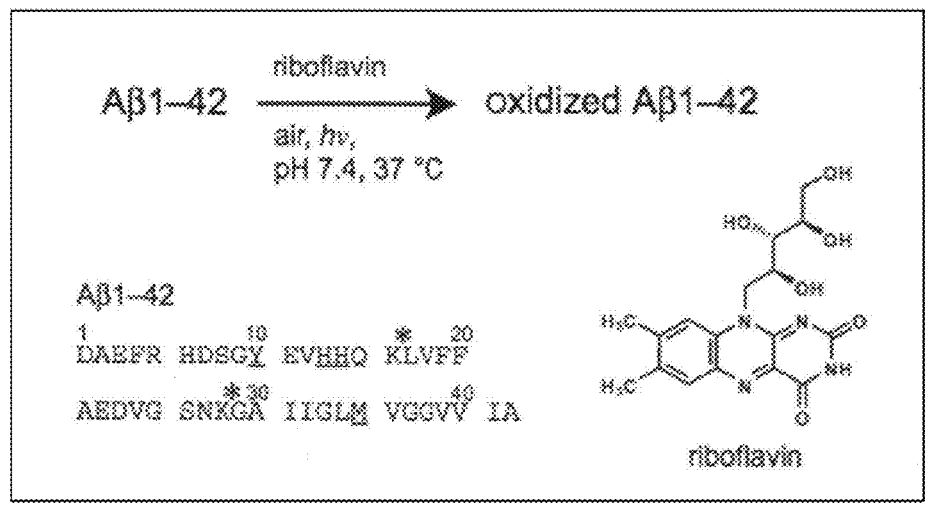
[Fig. 2]
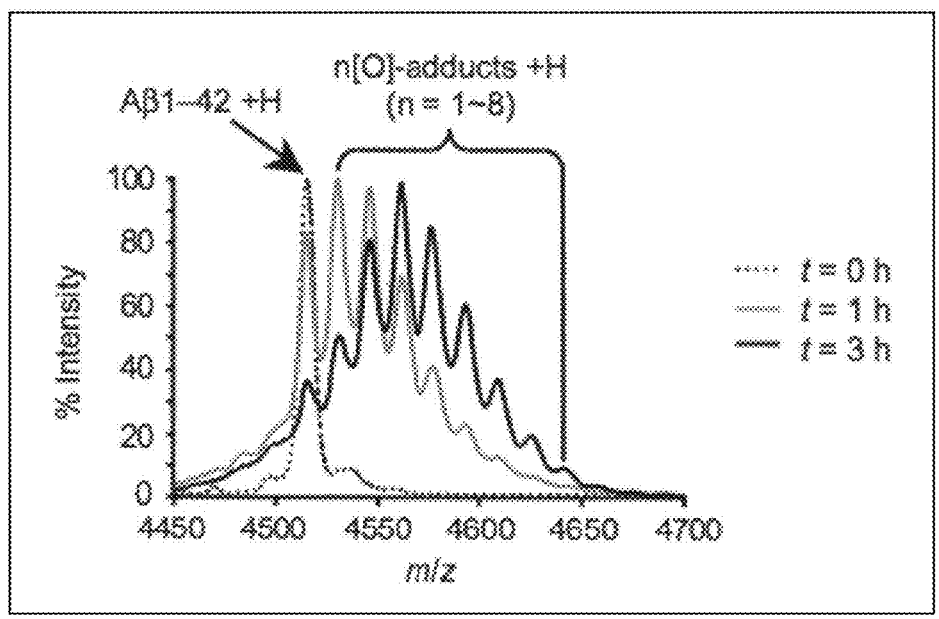

[Fig. 3]
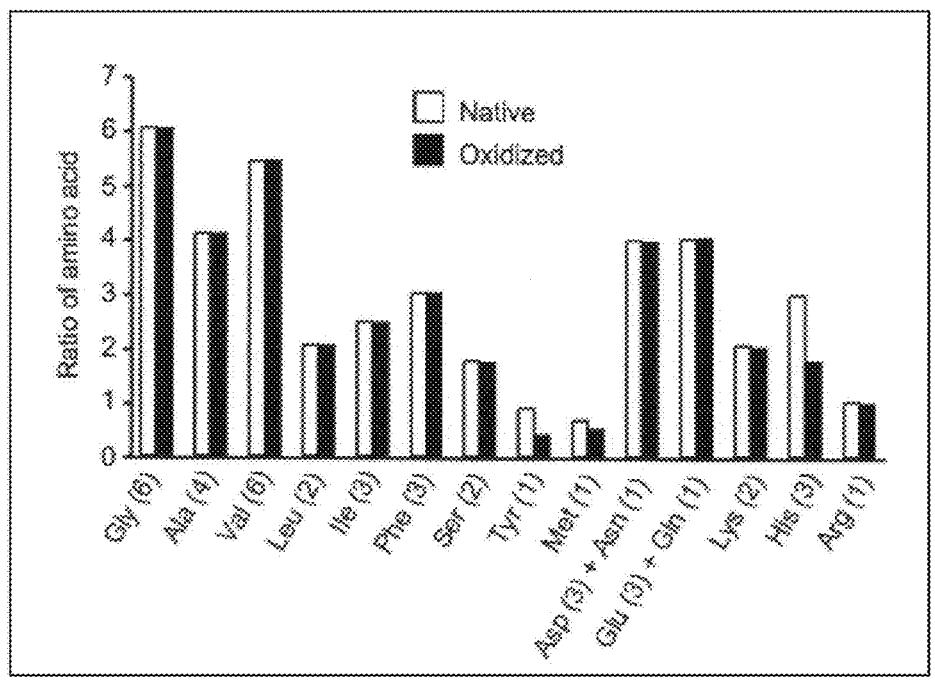
[Fig. 4]
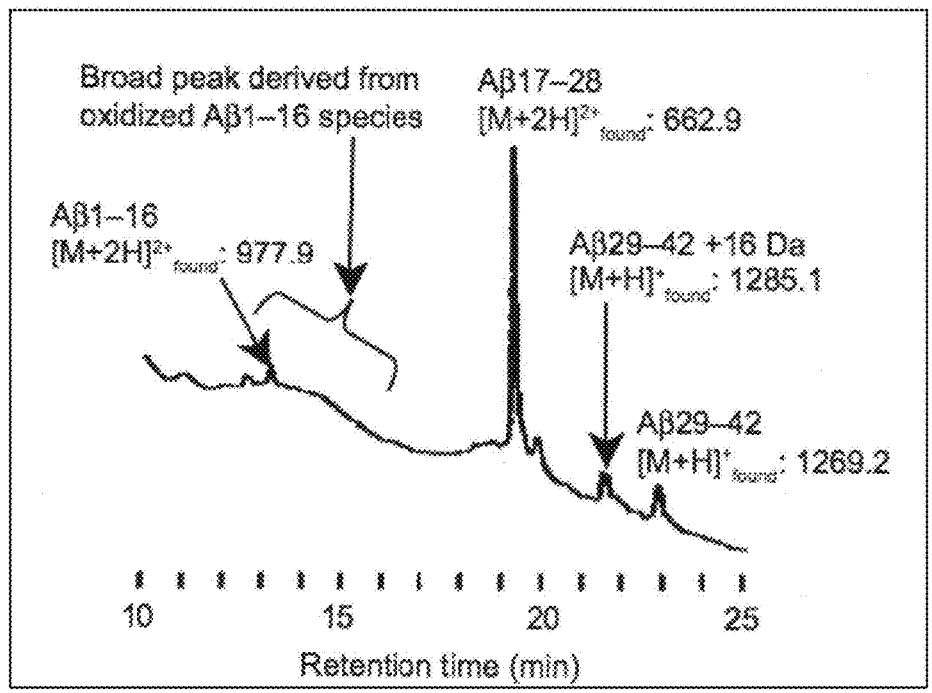

[Fig. 5]
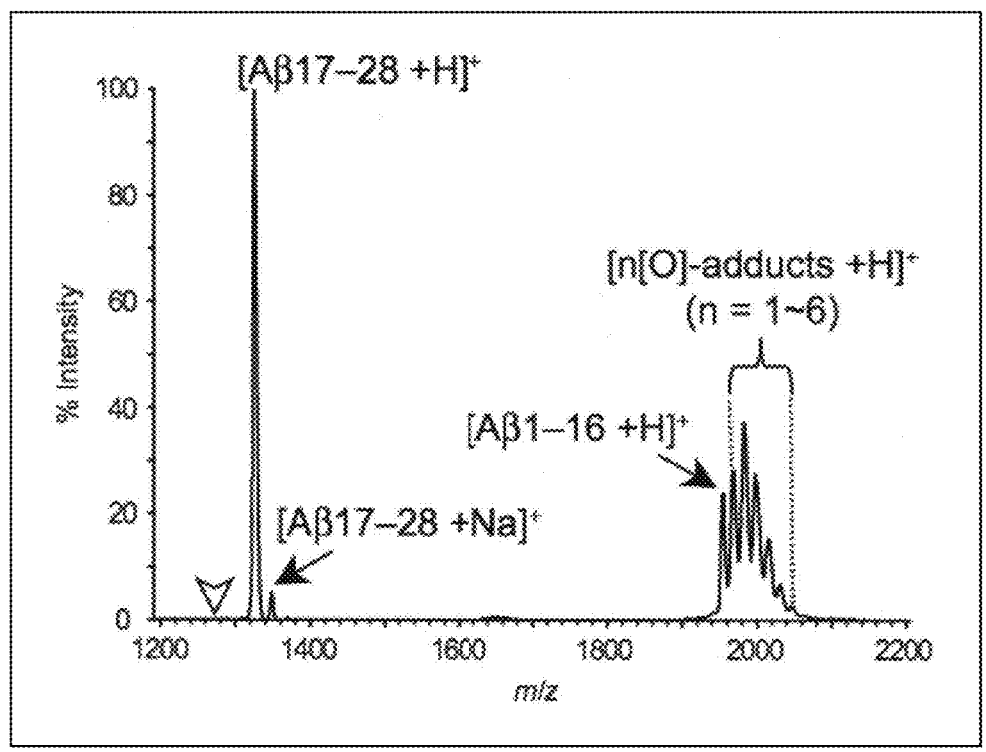

[Fig. 6]
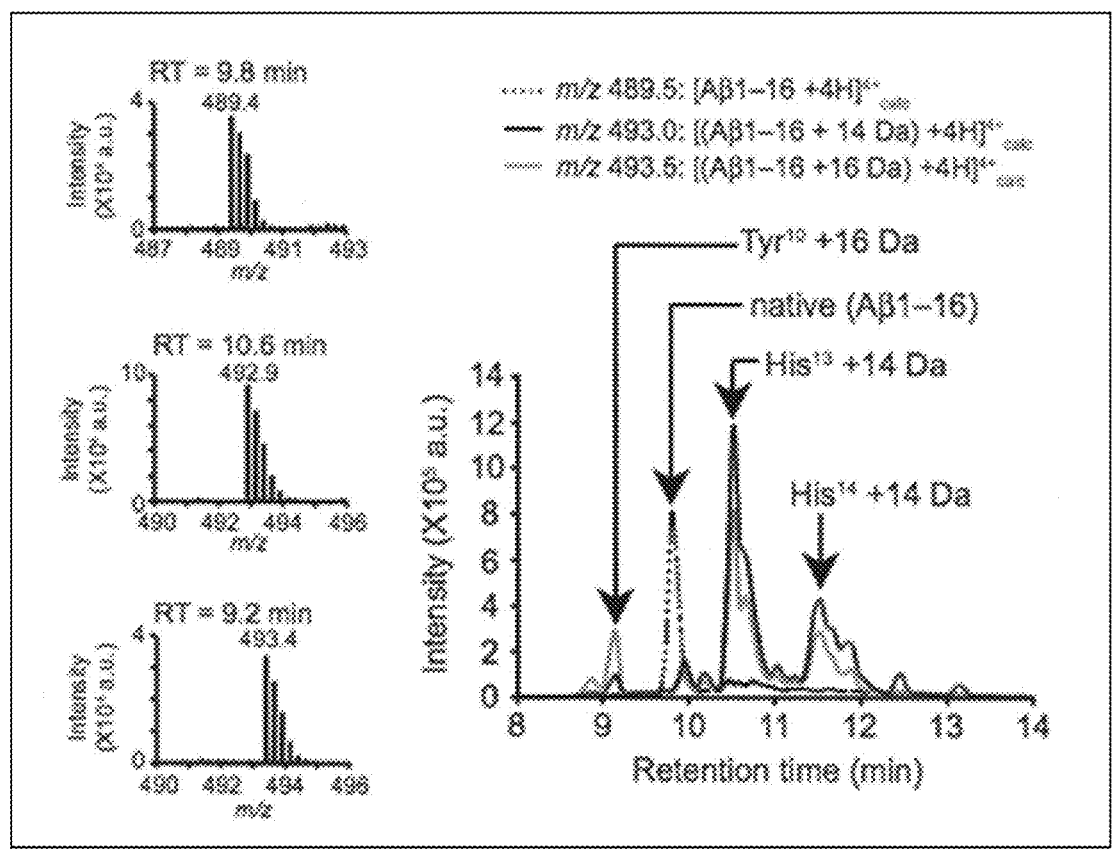

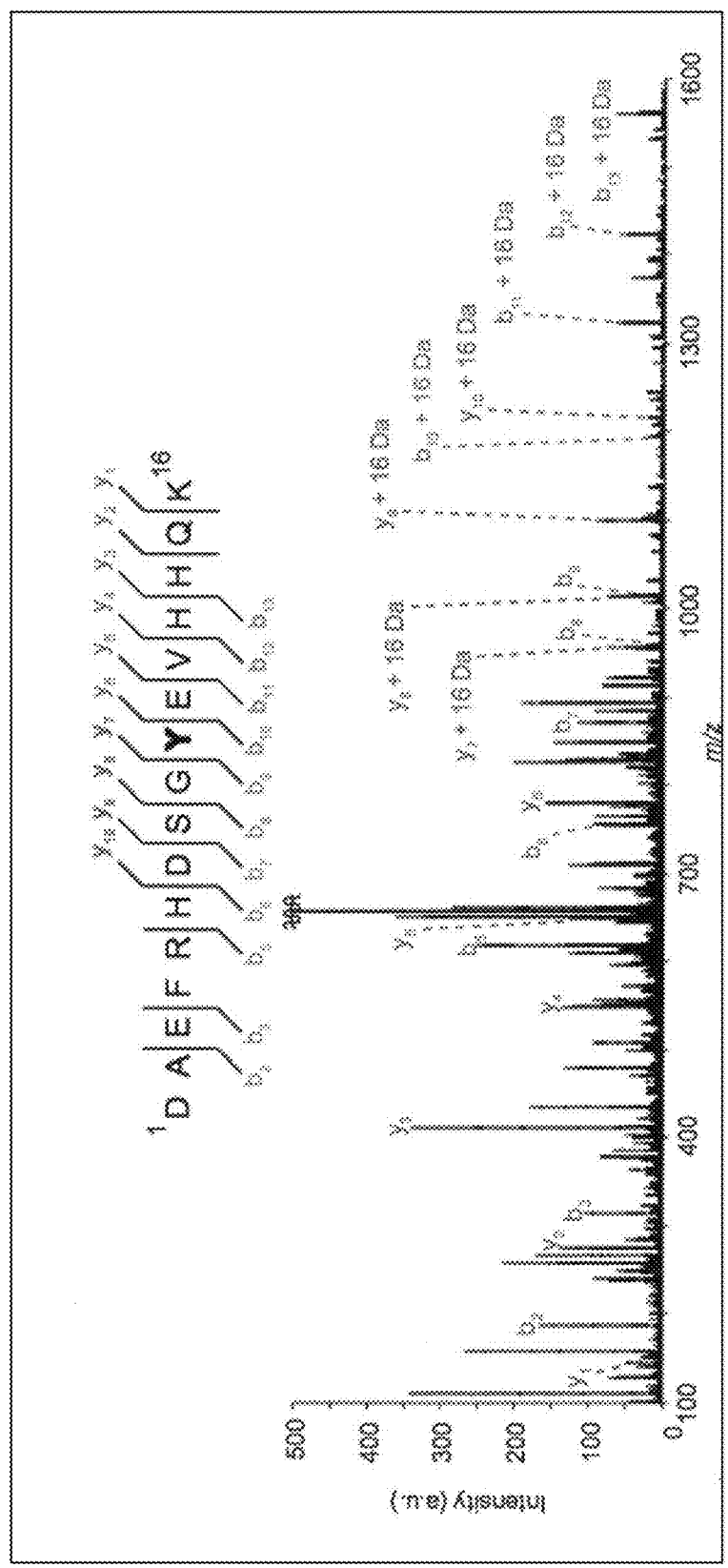
[Fig. 7]

[Fig. 8]
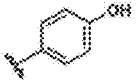

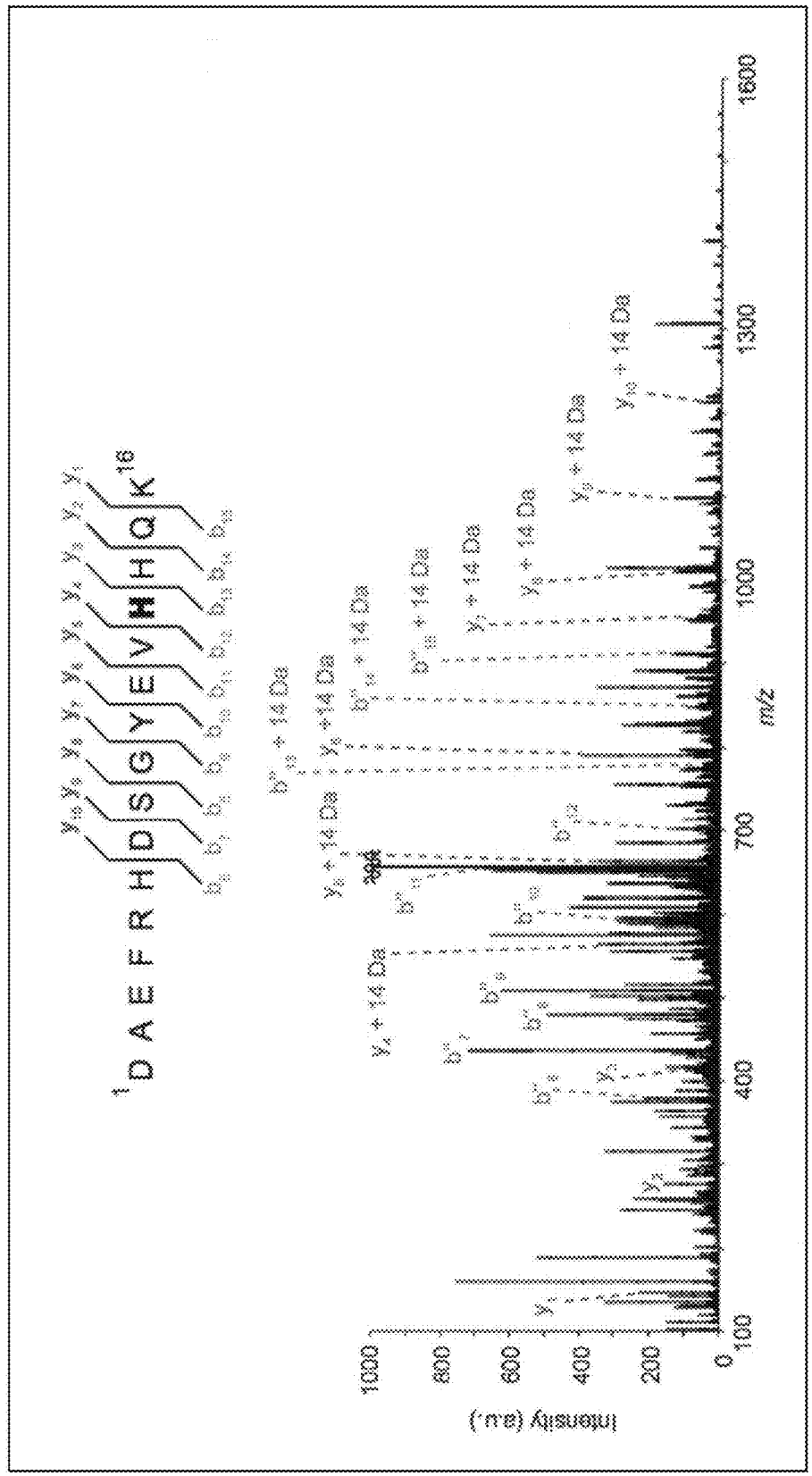
[Fig. 9]

[Fig. 10]
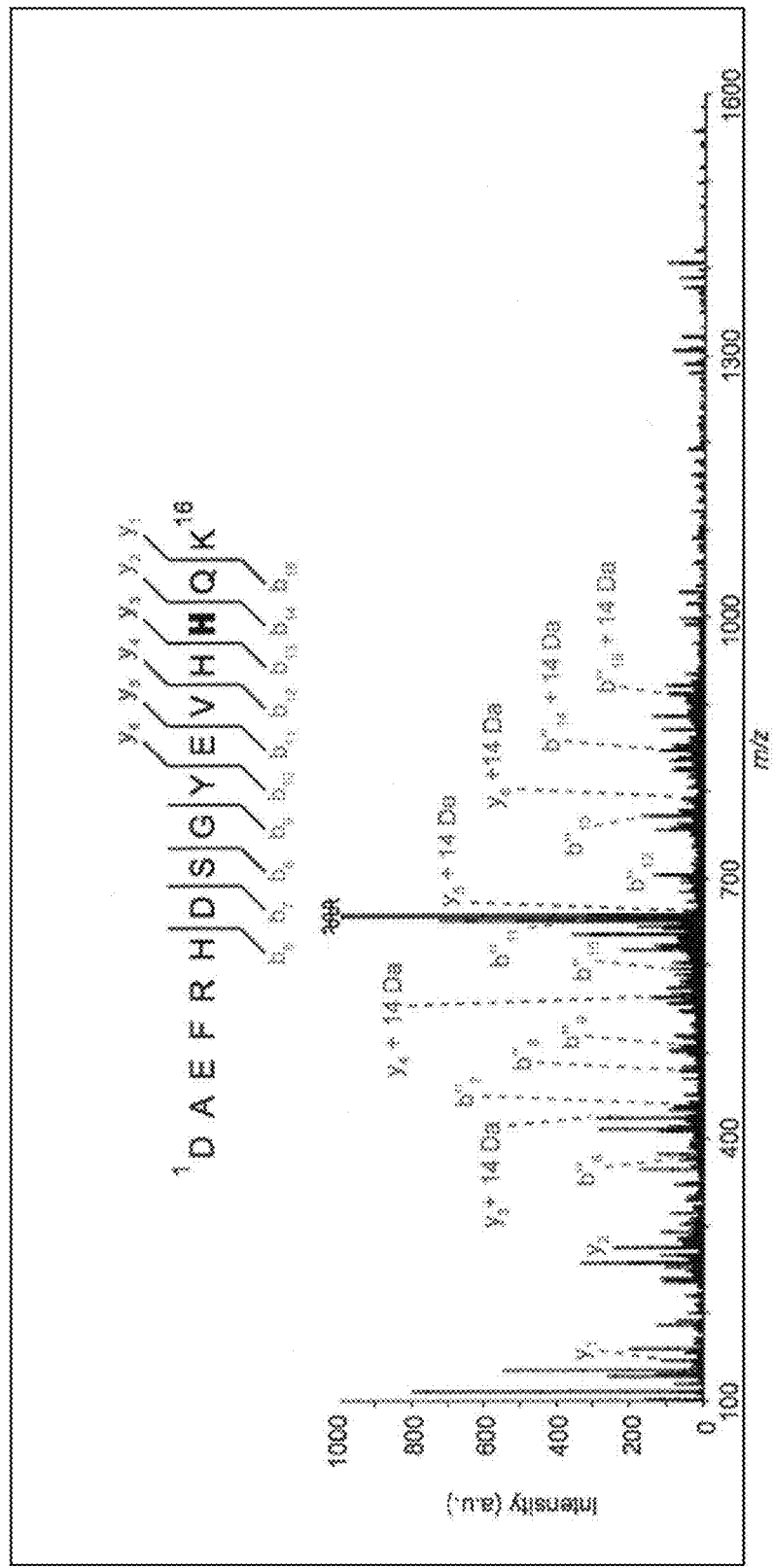

[Fig. 11]
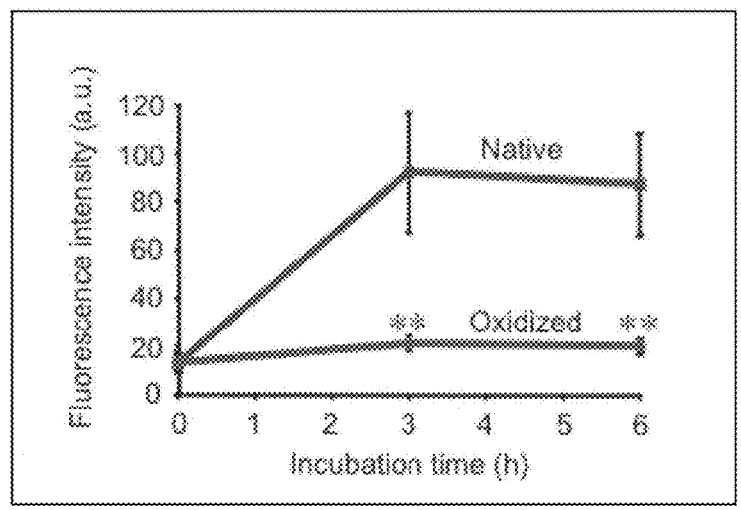
[Fig. 12]
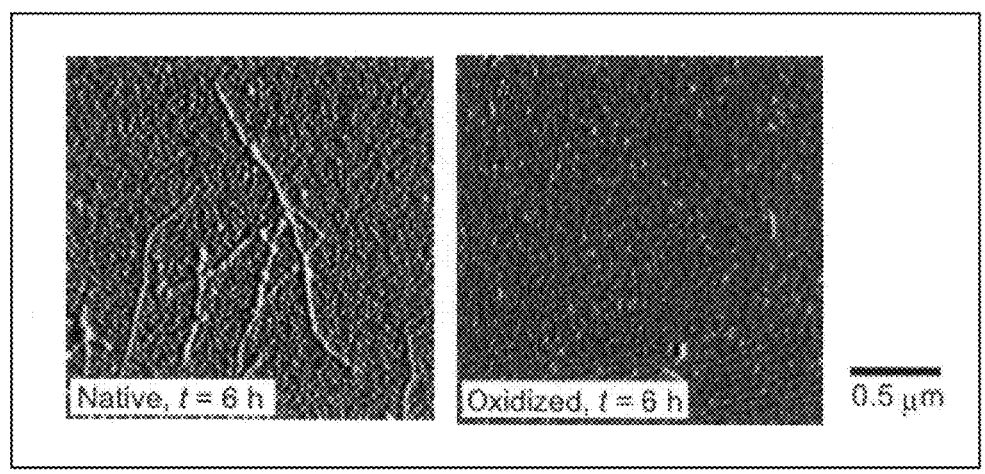

[Fig. 13]
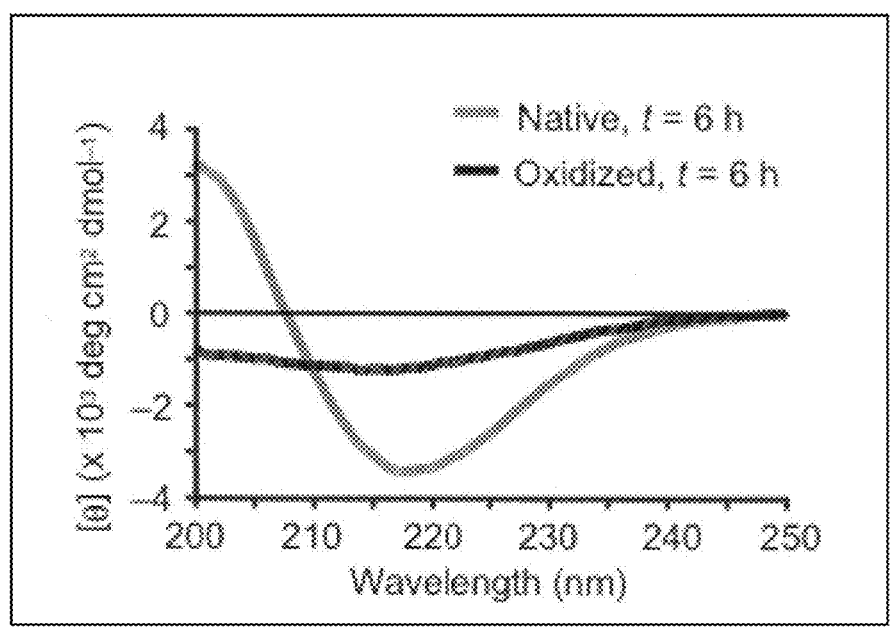

[Fig. 14]
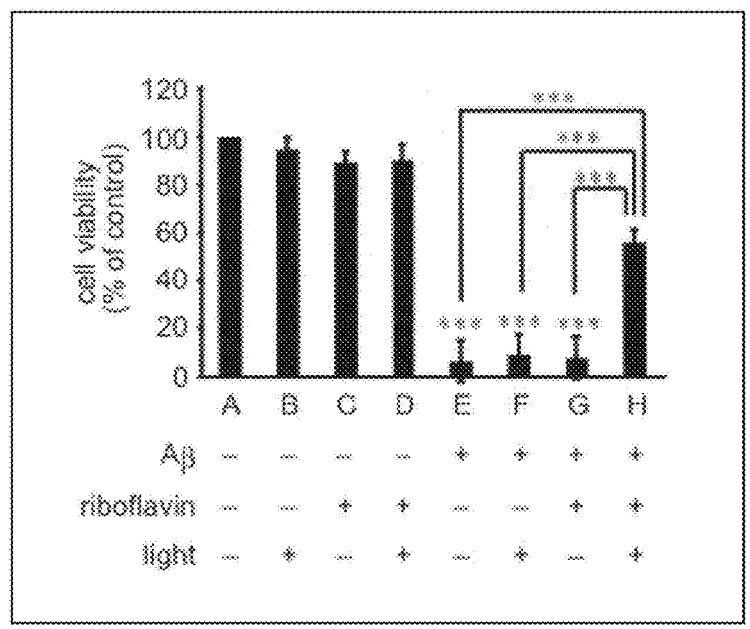
[Fig. 15]
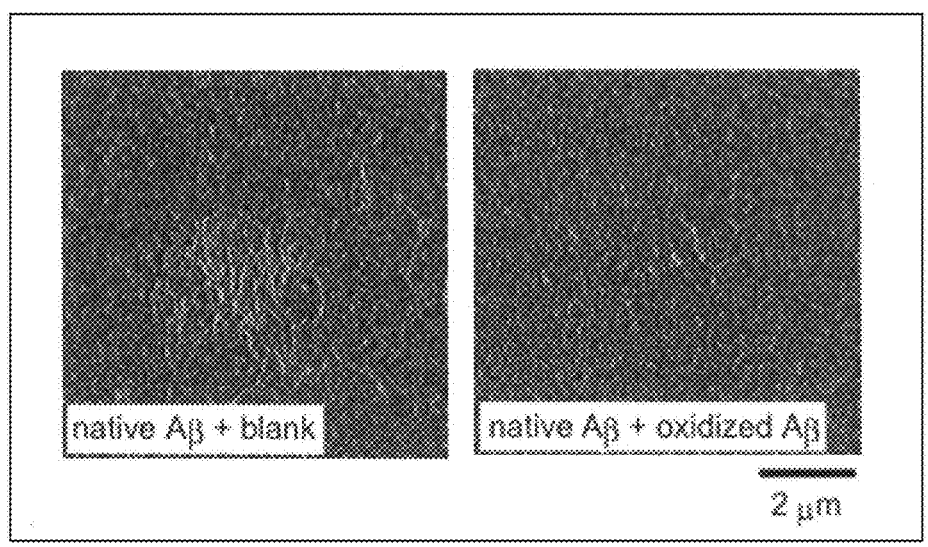

{Fig. 16}
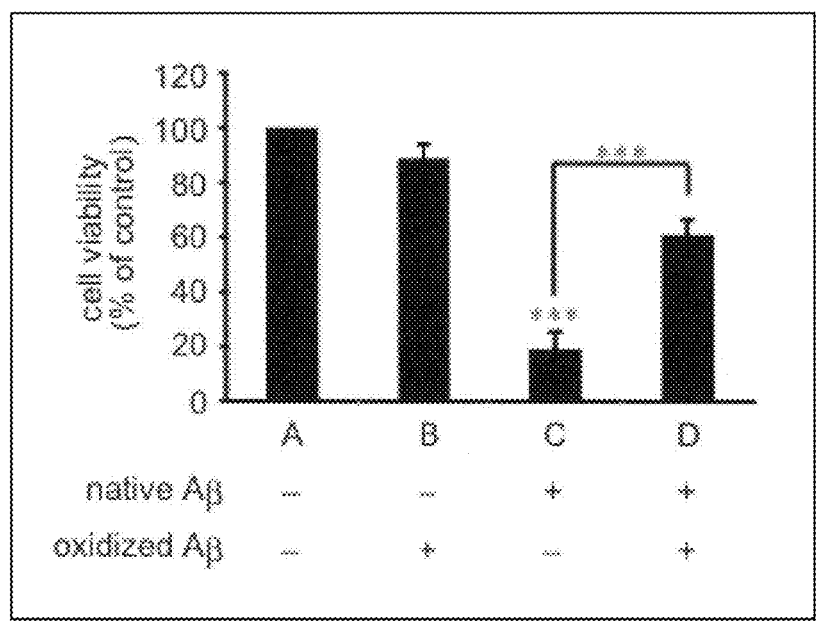

[Fig. 17]
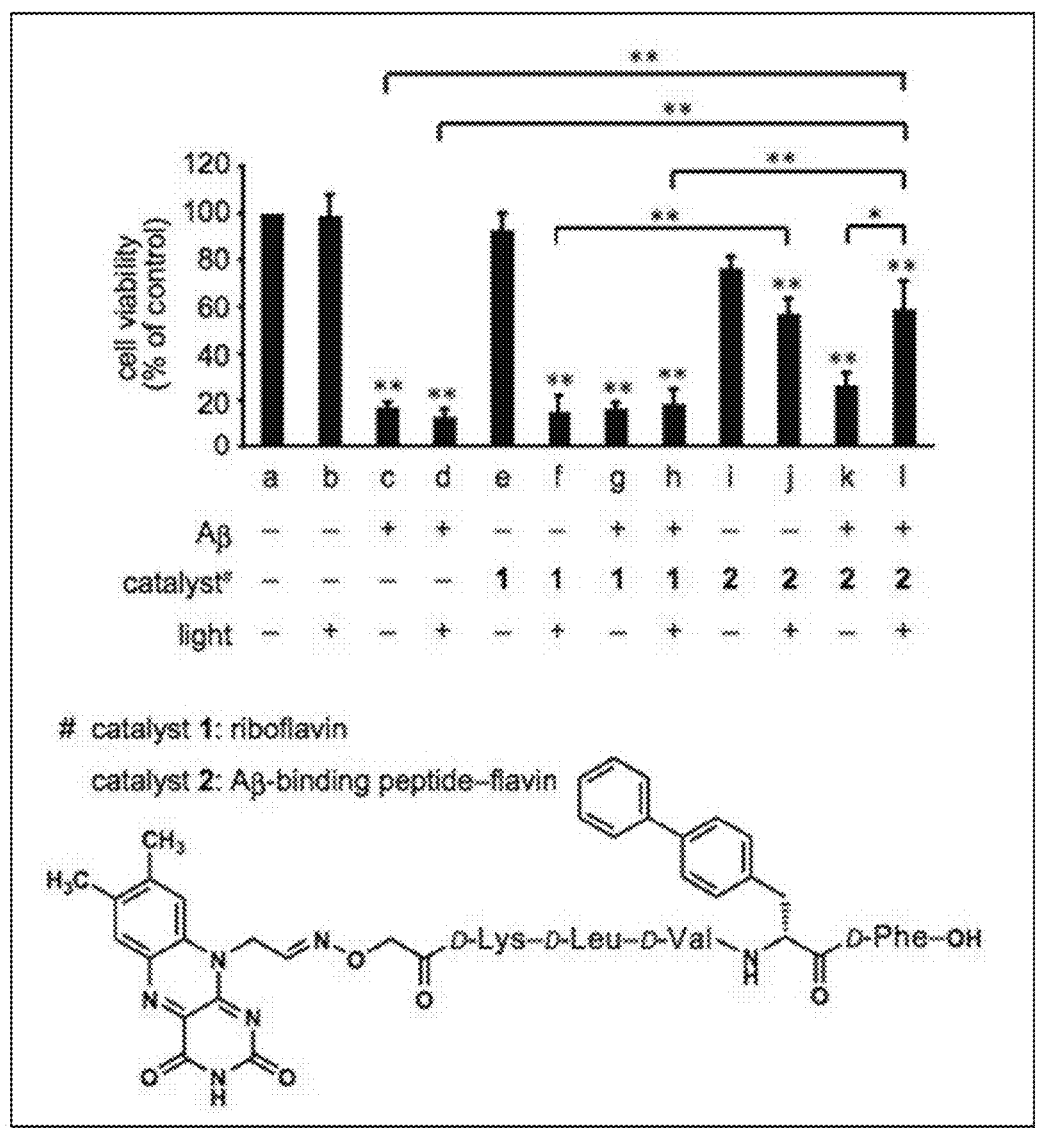

SEQUENCE LISTING

<160> NUMBER OF SEQ ID NOS: 3

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 5
<212> TYPE: PRT
<213> ORGANISM: Artificial sequence
<220> FEATURE:
<223> OTHER INFORMATION: Abeta binding peptide

<400> SEQUENCE: 2

Lys Leu Val Phe Phe
1               5

<210> SEQ ID NO 3
<211> LENGTH: 5
<212> TYPE: PRT
<213> ORGANISM: Artificial sequence
<220> FEATURE:
<223> OTHER INFORMATION: Abeta binding peptide
<220> FEATURE:
<221> NAME/KEY: MISC_FEATURE
<222> LOCATION: (4)..(4)
<223> OTHER INFORMATION: Xaa is phenyl phenylalanine

<400> SEQUENCE: 3

Lys Leu Val Xaa Phe
1               5

OXIDIZED Aβ PEPTIDE

TECHNICAL FIELD

The present invention relates to an oxidized Aβ peptide and to a preventive and/or therapeutic agent for Alzheimer's disease containing the oxidized Aβ peptide as an active ingredient.

BACKGROUND ART

Alzheimer's disease is a neurodegenerative disease having pathological characteristics of degeneration and loss of nerve cells, senile plaque formation, and neurofibrillary tangle. Alzheimer's disease induces a cognitive impairment that a memory, recognition, thinking, judgment, and the like are lost progressively, and finally leads to death.

The main substance of the senile plaque deposited in the brain is amyloid β peptide (Aβ peptide) composed of 39 to 43 amino acids. Aβ peptide shows cytotoxicity, and this is considered to induce Alzheimer's disease (Non-Patent Document 1). Aβ peptide secreted from cells is a polypeptide mainly composed of 40 or 42 amino acids. It is known that, among other Aβ peptides, an Aβ peptide composed of 42 amino acids is aggregated strongly, is deposited in the brain early, and has strong cytotoxicity (Non-Patent Document 2). Accordingly, a medical agent for inhibiting production of Aβ peptide and a medical agent for inhibiting aggregation of Aβ peptide are expected to be useful as a preventive and/or therapeutic agent for Alzheimer's disease.

Concerning a medical agent that inhibits production of Aβ peptide, studies have been focused on a substance capable of inhibiting β-secretase and γ-secretase, which are enzymes involved in production of Aβ peptide. In addition, an Aβ peptide degrading enzyme promoter, an anti-Aβ peptide antibody, a medical agent that inhibits aggregation of Aβ peptide, or the like have also been studied.

On the other hand, there have been reported that a Met-oxidized Aβ peptide (i.e., an oxidized product of Aβ peptide in which the sulfur atom of the Met residue has been oxidized) is present in a low amount in the living body, and the Met-oxidized product has lower aggregation than Aβ peptide (Non-Patent Documents 3 to 5).

CITATION LIST

Non-Patent Documents

Non-Patent Document 1: J. Hardy, D. J. Selkoe, Science 2002, 297, p 353.
Non-Patent Document 2: S. A. Gravina, et al. J. Biol. Chem., 1995, Vol. 270, p 7013
Non-Patent Document 3: Hou, L. et al. J. Biol. Chem., 2002, Vol. 277, No. 43, p 40173-40176
Non-Patent Document 4: Bitan, G. et al. J. Am. Chem. Soc., 2003, Vol. 125, No. 50, p 15359-15365
Non-Patent Document 5: Moskovitz, J. et al. Biochemistry, 2011, 50, p 10687-10697

SUMMARY OF THE INVENTION

Problems to be Solved by the Invention

However, existing inhibitors that inhibit enzymes involved in production of Aβ peptide cannot sufficiently inhibit production of Aβ peptide, whereas anti-Aβ peptide antibody has not been successfully developed for safety reasons.

Therefore, it is keenly demanded to develop a preventive and/or therapeutic agent for Alzheimer's disease by inhibiting aggregation of Aβ peptide and reducing toxicity of Aβ peptide from an entirely new viewpoint.

Means for Solving the Problems

In order to inhibit aggregation and to reduce toxicity, the prevent inventors have made extensive studies of artificial modification of Aβ peptide. Although Non-Patent Documents 3 to 5 describe that a Met-oxidized Aβ peptide present in vivo shows low aggregation by itself, the present inventors have reached new findings that a specific oxidized Aβ peptide obtained through artificial oxidation of Aβ peptide shows no aggregation by itself, strongly inhibits aggregation of native Aβ peptide, and decreases cytotoxicity of native Aβ peptide. Thus, the inventors have found the oxidized Aβ peptide is useful as a wholly new preventive and/or therapeutic agent for Alzheimer's disease, thereby completing the present invention.

Specifically, the present invention provides the following [1] to [30].

[1] An oxidized Aβ peptide wherein one or more amino acid residues of an Aβ peptide have been oxidized (excluding an oxidized Aβ peptide wherein only Met has been oxidized).

[2] The oxidized Aβ peptide according to [1], wherein one or more amino acid residues selected from the group consisting of at least Tyr and His have been oxidized.

[3] A drug, comprising the oxidized Aβ peptide according to [1] or [2].

[4] An Aβ peptide aggregation inhibitor, comprising the oxidized Aβ peptide according to [1] or [2] as an active ingredient.

[5] An Aβ peptide toxicity reducing agent, comprising the oxidized Aβ peptide according to [1] or [2] as an active ingredient.

[6] A preventive and/or therapeutic agent for Alzheimer's disease, comprising the oxidized Aβ peptide according to [1] or [2] as an active ingredient.

[7] A method of producing an oxidized Aβ peptide wherein one or more amino acid residues of an Aβ peptide have been oxidized (excluding an oxidized Aβ peptide wherein only Met has been oxidized), the method comprising oxidizing an Aβ peptide.

[8] The method of producing an oxidized Aβ peptide according to [7], wherein the oxidized Aβ peptide is an oxidized Aβ peptide wherein one or more amino acid residues selected from the group consisting of at least Tyr and His have been oxidized.

[9] A drug, comprising an oxidizing agent or oxidation catalyst for an Aβ peptide as an active ingredient.

[10] An Aβ peptide aggregation inhibitor, comprising an oxidizing agent or oxidation catalyst for an Aβ peptide as an active ingredient.

[11] An Aβ peptide toxicity reducing agent, comprising an oxidizing agent or oxidation catalyst for an Aβ peptide as an active ingredient.

[12] A preventive and/or therapeutic agent for Alzheimer's disease, comprising an oxidizing agent or oxidation catalyst for an Aβ peptide as an active ingredient.

[13] Use of the oxidized Aβ peptide according to [1] or [2] for producing a preventive and/or therapeutic agent for Alzheimer's disease.

[14] Use of the oxidized Aβ peptide according to [1] or [2] for producing an Aβ peptide aggregation inhibitor.
[15] Use of the oxidized Aβ peptide according to [1] or [2] for producing an Aβ peptide toxicity reducing agent.
[16] Use of an oxidizing agent or oxidation catalyst for an Aβ peptide for producing a preventive and/or therapeutic agent for Alzheimer's disease.
[17] Use of an oxidizing agent or oxidation catalyst for an Aβ peptide for producing an Aβ peptide aggregation inhibitor.
[18] Use of an oxidizing agent or oxidation catalyst for an Aβ peptide for producing an Aβ peptide toxicity reducing agent.
[19] The oxidized Aβ peptide according to [1] or [2] for use in preventing and/or treating Alzheimer's disease.
[20] The oxidized Aβ peptide according to [1] or [2] for use in inhibiting aggregation of an Aβ peptide.
[21] The oxidized Aβ peptide according to [1] or [2] for use in reducing toxicity of an Aβ peptide.
[22] An oxidizing agent or oxidation catalyst for an Aβ peptide for use in preventing and/or treating Alzheimer's disease.
[23] An oxidizing agent or oxidation catalyst for an Aβ peptide for use in inhibiting aggregation of an Aβ peptide.
[24] An oxidizing agent or oxidation catalyst for an Aβ peptide for use in reducing toxicity of an Aβ peptide.
[25] A method of inhibiting aggregation of an Aβ peptide, the method comprising administering the oxidized Aβ peptide according to [1] or [2].
[26] A method of reducing toxicity of an Aβ peptide, the method comprising administering the oxidized Aβ peptide according to [1] or [2].
[27] A method of preventing and/or treating Alzheimer's disease, the method comprising administering the oxidized Aβ peptide according to [1] or [2].
[28] A method of inhibiting aggregation of an Aβ peptide, the method comprising oxidizing an Aβ peptide.
[29] A method of reducing toxicity of an Aβ peptide, the method comprising oxidizing an Aβ peptide.
[30] A method of preventing and/or treating Alzheimer's disease, the method comprising oxidizing an Aβ peptide.

Effects of the Invention

By using the oxidized Aβ peptide according to the present invention, aggregation of Aβ peptide can be inhibited and toxicity of Aβ peptide can be reduced. Therefore, the oxidized Aβ peptide is useful for preventing and/or treating Alzheimer's disease. Also, by using the oxidizing agent or oxidation catalyst for an Aβ peptide, the oxidized Aβ peptide is produced in vivo or within cells, leading to inhibition of aggregation of Aβ peptide and reduction in toxicity of Aβ peptide. Thus, Alzheimer's disease can be prevented and/or treated.

BRIEF DESCRIPTION OF THE DRAWINGS

FIG. 1 shows oxidation reaction of Aβ1-42 using a photocatalyst, riboflavin. In the sequence of Aβ1-42, symbol * represents sites cleaved by Lys-C. Amino acids that were confirmed to have been oxidized in the present invention are underlined.
FIG. 2 shows the results of analysis of oxidation reaction of Aβ1-42 by using a mass spectrometer (MALD-TOF MS) t represents the reaction time.
FIG. 3 shows comparison between a native Aβ and an oxidized Aβ by amino acid analysis. The numbers in parentheses represent theoretical numbers of amino acids in Aβ. "Ratio of amino acid" represents a mole ratio of amino acids in a sample when phenylalanine is taken as 3.
FIG. 4 shows an LC chart obtained from LC/MS analysis after enzyme digestion. LC conditions: C18 reverse phase column (150 (4.6 mm), gradient mode of 0%-100% acetonitrile/0.1% aqueous TFA 40 min, flow rate of 0.9 mL min$^{-1}$, detection at UV 230 nm). Theoretical mass of Aβ fragment after enzyme digestion: Aβ1-16[M+2H]$^{2+}$: 977.9, Aβ17-28 [M+2H]$^{2+}$: 663.3, Aβ29-42[M+H]$^{+}$: 1269.8.
FIG. 5 shows the results of mass analysis (MALD-TOF MS) after enzyme digestion.
FIG. 6 shows the results of LC/MS/MS analysis of Aβ1-16 obtained after enzyme digestion. The left three charts are MS spectra at the retention time shown at the top of each chart. The right chart shows the results of extraction chromatography. LC conditions: C18 reverse-phase column (100 (1.0 mm, 40° C.) with a binary solvent system: linear gradient of 2%-42% acetonitrile in 0.1% aqueous formic acid over 20 min at a flow rate of 20 μL min$^{-1}$).
FIG. 7 shows the MS/MS spectrum of Aβ1-16+16 Da (peak at a retention time of 9.2 min in FIG. 6). Adduct of 16 Da was observed from $b_{10}$ to $b_{13}$ and $y_7$ to $y_{10}$ ions, whereas $b_2$ to $b_9$ (except for $b_4$) and $y_1$ to $y_6$ ions were intact, suggesting that +16 Da modification occurred at Tyr$^{10}$ residue.
FIG. 8 shows (estimated) structures of oxidative modification products of tyrosine and histidine.
FIG. 9 shows the MS/MS spectrum of Aβ1-16+14 Da (peak at a retention time of 10.6 min in FIG. 6). Adduct of 14 Da was observed from $b_{13}$ to $b_{15}$ and $y_4$ to $y_{10}$ ions, whereas $b_6$ to $b_{12}$ and $y_1$ to $y_3$ ions were intact, suggesting that +14 Da modification occurred at His$^{13}$ residue.
FIG. 10 shows the MS/MS spectrum of Aβ1-16+14 Da (peak at a retention time of 11.5 min in FIG. 6). Adduct of 14 Da was observed from $b_{14}$ and $b_{15}$ and $y_3$ to $y_6$ ions, whereas $b_6$ to $b_{13}$ and $y_1$ and $y_2$ ions were intact, suggesting that +14 Da modification occurred at His$^{14}$ residue.
FIG. 11 shows the results of thioflavin T fluorescence assay. (n=6, mean ((SD; **p<0.01 versus native Aβ1-42 by Student's t-test).
FIG. 12 shows the results of atomic force microscope analysis. Native Aβ is shown left, and oxidized Aβ is shown right, and t represents the reaction time.
FIG. 13 shows the results of circular dichroism spectroscopy analysis. t represents the reaction time.
FIG. 14 shows comparison in terms of toxicity between native Aβ (E, F, G) and oxidized Aβ (H) using PC12 cells. The vertical axis represents cell viability (n=5, mean±SEM; ***p<0.001 versus A or in indicated pair by Tukey's test).
FIG. 15 shows the results of atomic force microscope analysis. The sole native Aβ is shown left. Native Aβ+oxidized Aβ is shown right.
FIG. 16 shows comparison in terms of toxicity between solo native Aβ (C) and native Aβ+oxidized Aβ (D) using PC12 cells. The vertical axis represents cell viability (n=6, mean±SEM; ***p<0.001 versus A or in indicated pair by Tukey's test).
FIG. 17 shows the evaluation results of cell viability by photo-oxygenation reaction in the presence of cells. Aβ is native Aβ. Catalyst 1 is riboflavin. Catalyst 2 is Aβ high-affinity peptide-bonded flavin. The vertical axis represents cell viability.

MODES FOR CARRYING OUT THE INVENTION

The oxidized Aβ peptide according to the present invention is an Aβ peptide in which one or more amino acid residues of an Aβ peptide have been oxidized (excluding an oxidized Aβ peptide in which only Met has been oxidized).

The Aβ peptide has an amino acid sequence (1-42) represented by SEQ ID NO: 1 or an amino acid sequence (1-40) of the sequence shown by SEQ ID NO: 1.

In the oxidized Aβ peptide according to the present invention, one or more amino acid residues of 40 or 42 amino acid residues of the Aβ peptide have been oxidized.

Preferably, the oxidized Aβ peptide is one in which one or more amino acid residues selected from the group consisting of at least Tyr and His have been oxidized. If one or more amino acid residues selected from the group consisting of Tyr and His have been oxidized, oxidized Aβ peptides in which Met has been further oxidized fall within the scope. Examples of the preferable oxidized Aβ peptide include a Tyr-oxidized Aβ peptide, a His-oxidized Aβ peptide, a Tyr and His-oxidized Aβ peptide, a Tyr and Met-oxidized Aβ peptide, a His and Met-oxidized Aβ peptide, a Tyr, His and Met-oxidized Aβ peptide, and a combination thereof. Since merely a single Tyr and a single Met are present in the SEQ ID NO: 1, the Tyr and the Met are oxidized. On the other hand, since 6His, 13His and 14His are present as to His, all His's may be oxidized, more preferably, 13His and 14His are oxidized. Oxidation is preferably achieved by oxygen. Specifically, a hydroxyl group or oxo group (oxide) is more preferably added to each amino acid residue.

From the mass spectrum analysis of the above-described amino acid residue-oxidized products, in the case of Tyr, it is estimated that a phenyl group of a tyrosine residue has been substituted with two or three hydroxyl groups (dihydroxyphenyl group, trihydroxyphenyl group). In the case of His, it is estimated that an imidazole ring of a histidine residue has been oxidized, that is, the histidine residue has a dehydroimidazolone ring or a hydroxyimidazolone ring. In the case of the Met, it is estimated that oxygen has been added to a sulfur atom of a methionine residue.

The oxidized Aβ peptide according to the present invention may be produced by, for example, oxidizing an Aβ peptide. Oxidation reaction may be such that oxygen atoms are supplied to the amino acid residues of the Aβ peptide. Examples of the oxidation reaction include a method in which the Aβ peptide is irradiated with light in the presence of oxygen and an oxidation catalyst such as riboflavin, thioflavin T, Congo red, methylene blue, rose bengal, an acridine derivative, porphyrin and a metal complex thereof (metal=iron, manganese, zinc), a ruthenium tris(bipyridine) complex, and a compound produced by bonding an Aβ peptide affinity molecule to these molecules; and a method in which the Aβ peptide is reacted with an oxidizing agent such as a peroxide, hypervalent iodine, and perchloric acid.

In the method of using an oxidation catalyst, since oxygen in air or in a solution is consumed, the Aβ peptide and the oxidation catalyst may be added to a container, and light may be applied thereto for reaction. The light may be chosen based on the type of the oxidation catalyst. This scheme is particularly preferable because the reaction proceeds under physiological conditions, for example, at 30 to 40° C.

In the method of using an oxidizing agent, the oxidizing agent may be added to a solution containing the Aβ peptide to carry out the reaction.

The oxidized Aβ peptide according to the present invention shows an excellent action for inhibiting aggregation of the Aβ peptide and an excellent action for reducing toxicity of the Aβ peptide as shown in Examples hereinbelow. Therefore, the oxidized Aβ peptide according to the present invention is useful as an Aβ peptide aggregation inhibitor, an Aβ peptide toxicity reducing agent, and a preventive and/or therapeutic agent for a disease accompanied by amyloid deposition and Aβ peptide aggregation in animals including a human, e.g., Alzheimer's disease and the Down's Syndrome.

When the Aβ peptide is oxidized in vivo or within cells, the oxidized Aβ peptide according to the present invention is generated in vivo or within cells. By the oxidized Aβ peptide according to the present invention, it is possible to inhibit aggregation of the Aβ peptide, to lower the toxicity of the Aβ peptide, and to prevent and/or treat Alzheimer's disease.

In order to oxidize Aβ peptides in vivo or within cells, the oxidizing agent or oxidation catalyst may be introduced in vivo or into cells to induce oxidation reaction. Examples of the oxidizing agent used herein include the oxidizing agents listed in the case of producing oxidized Aβ peptides, e.g., peroxide, hypervalent iodine, and perchloric acid. Also, the reaction using an oxidation catalyst and light may be employed. Light may be applied in a similar manner to a photodynamic therapy procedure, for example.

Specifically, the oxidation catalyst may be introduced in vivo or into cells. Once the oxidation catalyst reaches the target site, light may be irradiated. A way to administer the oxidation catalyst or oxidizing agent in vivo includes intramuscular injection, intravenous injection, local administration, and oral administration.

In order to selectively oxidize Aβ peptides in vivo or within cells, a riboflavin derivative may be synthesized by bonding a molecule having affinity with Aβ peptide to riboflavin or thioflavin T, and the Aβ peptide may be reacted with the riboflavin derivative. Examples of the Aβ peptide affinity molecule include thioflavin T, Congo red, a stilbene derivative, a polythiophene derivative, an acridine derivative, an aminonaphthyl derivative, a Lys-Leu-Val-Phe-Phe (SEQ ID NO: 2) derivative, curcumin, myricetin, rifampicin and nordihydroguaiaretic acid.

A component that causes production of oxidized Aβ peptides in vivo or within cells, i.e., an oxidizing agent or oxidation catalyst, is useful as an Aβ peptide aggregation inhibitor, an Aβ peptide toxicity reducing agent, and a preventive and/or therapeutic agent for Alzheimer's disease.

A drug according to the present invention contains the oxidized Aβ peptide or the oxidizing agent or oxidation catalyst for an Aβ peptide as an active ingredient.

If the oxidized Aβ peptide or the oxidizing agent or oxidation catalyst for an Aβ peptide according to the present invention is used as a therapeutic agent for humans, the daily dose for an adult is 1 mg to 1 g, preferably 10 mg to 300 mg.

A pharmaceutical composition containing the oxidized Aβ peptide or the oxidizing agent or oxidation catalyst for an Aβ peptide according to the present invention may be prepared through a preparation method employed for a variety of drug formulations by selecting an appropriate drug formulation depending on the administration route and using a pharmaceutically acceptable carrier. Examples of the dosage form of the pharmaceutical composition containing the product of the present invention as a main component include oral drug formulations such as tablets, powders, granules, capsules, liquids, syrups, elixirs, and oil or aqueous suspensions.

When an injection is prepared, a stabilizer, a preservative, and a solubilizing agent may be added to the drug formulation. A solution that sometimes contains such an adjuvant may be stored in a container and then subjected to lyophilization or the like to form a solid drug formulation which is prepared just before use. A single dose may be stored in one container. Also, a multiple dosage may be stored in one container.

Examples of an external preparation include liquid formulations, suspensions, emulsions, ointments, gels, creams, lotions, sprays, and patches.

A solid drug formation contains a pharmaceutically acceptable additive together with the oxidized Aβ peptide or the oxidizing agent or oxidation catalyst for an Aβ peptide according to the present invention. For example, fillers, extenders, binders, disintegrants, dissolution promoters, wetting agents, and lubricants may be chosen as needed and mixed for drug formation.

Examples of a liquid formulation include solutions, suspensions, and emulsions, and the liquid formulation may include a suspending agent, an emulsifying agent or the like as an additive.

EXAMPLES

Hereinafter, the present invention will be described in detail by way of Examples. It should be noted that the scope of the present invention is not limited to the Examples described below.

Example 1

Details of Each Experimental Method (1) Experiments of Thioflavin T Assay

A phosphate buffer (10 mM, pH 7.4) in which Aβ1-42 (20 µM) and riboflavin (4 µM) had been dissolved was incubated at 37° C. under irradiation with a fluorescent lamp (24 W, natural white, a distance between a light source and a reaction mixture was about 3 cm). A part of the reaction mixture (10 µL) was added to a 50 mM glycine-NaOH buffer (pH 8.5, 400 µL) containing thioflavin T (5 µM), and the resultant mixture was immediately mixed to measure a fluorescence intensity of thioflavin T. In the fluorescence intensity measurement, an excitation wavelength was 440 nm, and a fluorescence wavelength was 470 nm.

(2) Experiments of Atomic Force Microscope Analysis

A phosphate buffer (10 mM, pH 7.4) in which Aβ1-42 (20 µM) and riboflavin (4 µM) had been dissolved was incubated at 37° C. under irradiation with a fluorescent lamp (24 W, natural white, a distance between a light source and a reaction mixture was about 3 cm). A part of the reaction mixture (10 µL) was added on mica, incubated at room temperature for 3 minutes, washed with 20 µL of water, and air dried. The measurement was carried out using Nano Wizard II (JPK instruments AG, Berlin, Germany) in a tapping mode in air at room temperature.

(3) Experiments of Circular Dichroism Spectroscopy Analysis

A phosphate buffer (10 mM, pH7.4) in which Aβ1-42 (20 µM) and riboflavin (4 µM) had been dissolved was incubated at 37° C. under irradiation with a fluorescent lamp (24 W, natural white, a distance between a light source and a reaction mixture was about 3 cm). A part of the reaction mixture was analyzed using Model 202SF (AVIV Biomedical, Inc., Lakewood, N.J.).

(4) Cell Experiments

PC12 cells, i.e., rat adrenal medulla-derived pheochromocytoma (purchased from RIKEN, Japan), were used. A phosphate buffer (pH 7.4) in which Aβ1-42 (20 µM) and riboflavin (4 µM) had been dissolved was incubated at room temperature under irradiation with a fluorescent lamp (24 W, natural white, a distance between a light source and a reaction mixture was about 3 cm). A part of the reaction mixture (50 µL) was added to a cell culture medium (50 µL) (final Aβ concentration was 10 µM), and the mixture was incubated at 37° C. for 48 hours under 5% $CO_2$ atmosphere. Cells were observed and photographed using an inverted microscope DMI6000 B (Leica Microsystems GmbH, Wetzlar, Germany) equipped with a digital camera DFC360 FX (Leica Microsystems GmbH). A cell count reagent containing WST-8 (2-(2-methoxy-4-nitrophenyl)-3-(4-nitrophenyl)-5-(2,4-disulfonyl)-2H-tetrazolium, monosodium salt) (10 µL) was added to the mixture. The mixture was incubated at 37° C. for 6 hours under 5% $CO_2$ atmosphere. Thereafter, absorbance at 450 nm (reference wavelength: 655 nm) was measured by iMark™ plate reader (Bio-Rad Laboratories, Inc., Hercules, Calif.).

Example 2

Oxidation Reaction

A phosphate buffer (10 mM, pH 7.4) in which Aβ3-42 (SEQ ID NO: 1) (2 µM) and riboflavin (4 µM) had been dissolved was incubated at 37° C. under irradiation with a fluorescent lamp (24 W, natural white, a distance between a light source and a reaction mixture was about 3 cm) (FIG. 1), and the reaction was monitored by a mass spectrometer (MALD-TOF MS) (FIG. 2). After the reaction was carried out for 3 hours, along with disappearance of the raw material Aβ1-42, it was observed a spectrum of oxidized Aβ to which one to eight oxygen atoms were added. The same sample was analyzed for amino acids. As a result, the amounts of tyrosine and histidine were decreased to about half of a non-oxidized control sample (FIG. 3). By the same analysis, it was also observed that the amount of methionine was slightly decreased. The results revealed that the oxidation reactions of tyrosine, histidine, and methionine proceeded. Thus, by the results of a mass spectrometry measurement, it was found that almost Aβ1-42 was oxidized after the reaction for 3 hours.

In order to analyze the oxidized structure in more detail, a sample of the oxidized Aβ1-42 was digested by enzyme, i.e., endopeptidase Lys-C (cleaving on the C terminal side of Lys (see FIG. 1), purchased from Hoffmann-La Roche Ltd., Basel, Switzerland) (Aβ was reacted with 1/50 amount of the enzyme at 37° C. for about 12 hours). The resultant digested material was analyzed by LC/MS (ESI-TOF) and the mass spectrometer (MALD-TOF MS). In the LC/MS analysis, a 16 Da adduct of Aβ29-42 was detected (FIG. 4). This result and the results of the former amino acid analysis indicate that a methionine side chain at position 35 was oxidized to a sulfoxide. By the mass spectrometer (MALD-TOF MS), Aβ17-28 was detected, and no oxygen atom adduct was observed (FIG. 5). It shows that Aβ17-28 was not oxidized. On the other hand, the mass spectrometer (MALD-TOF MS) shows a peak group corresponding to adducts in which one to six oxygen atoms were added to Aβ1-16 (FIG. 5). Furthermore, Aβ1-16 was analyzed by LC/MS/MS (ESI-Qq-TOF). As a result, a 16 Da adduct of Aβ1-16 was detected (FIG. 6, left lower spectrum diagram), and the peak at a retention time of 9.2 min (FIG. 6, right spectrum) was found to be derived from molecule species in which tyrosine at position 10 was modified by +16 Da (FIG. 7). It may be conceivable that tyrosine was oxidized to 3,4-dihyroxyphenylalanine (FIG. 8). By the LC/MS/MS (ESI-Qq-TOF) analysis, a 14 Da adduct of Aβ1-16 was also detected (FIG. 6, left center spectrum), and it was suggested that the peaks at a retention time of 10.6 min and a retention time of 11.5 min (FIG. 6, right spectrum) correspond to 14 Da adducts of histidine at position 13 and histidine at position 14, respectively (FIG. 9 and FIG. 10, respectively). It may be conceivable that histidine was oxidized to a dehydro-2-imidazolone derivative (FIG. 8). Also, a 28 Da adduct, a 30 Da adduct, and a 44 Da adduct were detected. It is conceivable that these are derived from multiple oxidation of tyrosine at position 10, histidine at position 13, and histidine at position 14. In view of the peak group corresponding to the adducts in which one to six oxygen atoms were added shown by the mass spectrometry (MALD-TOF MS), it suggests the presence of the compound in which a plurality of oxygen atoms are added to one tyrosine or histidine. For example, estimated is 3,4,5-trihydroxyphenylalanine in the case of tyrosine or hydroxy-2-imidazolone derivative in the case of histidine (FIG. 8). (See 1) Pattison, D. I., Rahmanto, A. S. & Davies, M. J. Photo-oxidation of proteins. Photochem. Photobiol. Sci. 11, 38-53 (2012). 2) Schey, K. L. & Finley, E. L. Identification of peptide oxidation by tandem mass spectrometry. Acc. Chem. Res. 33, 299-306 (2000)). As described above, by a riboflavin catalyst system, it was confirmed that the oxidation reactions of tyrosine at position 10, histidine at position 13, histidine at position 14, and methionine at position 35 proceeded.

Example 3

Investigation of Aggregation

A phosphate buffer (10 mM, pH 7.4) in which Aβ1-42 (20 µM) and riboflavin (4 µM) had been dissolved was incubated at 37° C. under irradiation with a fluorescent lamp (24 W, natural white, a distance between a light source and a reaction mixture was about 3 cm) to provide a sample "oxidized Aβ". A phosphate buffer having the same composition was reacted with no irradiation to provide a sample "native Aβ" as a control. Aggregation of each sample was evaluated by thioflavin T assay (it is known that fluorescence intensity of thioflavin T corresponds to the amount of an aggregate being rich in β sheet structure) (FIG. 11). At the incubation time of 3 hours and 6 hours, the fluorescence intensity of thioflavin T of the oxidized Aβ was significantly lower than that of the native Aβ. The results suggest that the oxidized Aβ has low aggregation. By the atomic force microscope analysis, fibril formation was clearly observed in the native Aβ, but hardly in the oxidized Aβ (FIG. 12). Furthermore, by the circular dichroism spectroscopy analysis, it was found that there was a transition from a random coil structure to a β sheet structure in the native Aβ, but the random coil structure was maintained in the oxidized Aβ (FIG. 13).

Example 4

Investigation of Cytotoxicity

PC12 cells, i.e., rat adrenal medulla-derived pheochromocytoma (neural model cells), were used to compare cytotoxicity of the native Aβ and the oxidized Aβ (FIG. 14). In the presence of the native Aβ (10 µM), 90% or more of the cells died. In contrast, in the presence of the oxidized Aβ (10 µM), a cell viability of 50% or more was maintained. Only in the presence of the native Aβ, an apoptotic cell death was observed. The results show that the oxidative modification significantly lowered the cytotoxicity.

Example 5

Inhibition of Aggregation and Cytotoxicity of Native Aβ

By the atomic force microscope analysis, when the native Aβ (20 µM) was incubated (37° C., 6 hours) in the coexistence of the oxidized Aβ (20 µM), an amyloid fibril content was significantly decreased as compared with the case of the native Aβ (20 µM) alone (FIG. 15). The results show that the oxidized Aβ inhibited the aggregation of the native Aβ. In the presence of the native Aβ (10 µM), the cell viability of the PC 12 cells was about 20%. In contrast, when the oxidized Aβ (10 µM) coexisted with the native Aβ (10 µM), the cell viability was 60% or more (FIG. 16). The results show that the oxidized Aβ inhibited the cytotoxicity of the native Aβ.

Example 6

PC12 cells, i.e., rat adrenal medulla-derived pheochromocytoma (purchased from RIKEN, Japan), were used. In a plate well in which the PC12 cells had been seeded, a phosphate buffer (pH 7.4, 50 µL) containing 20 µM of Aβ and a catalyst (Catalyst 1 in 4 µM or Catalyst 2 in 20 µM) was irradiated with 500 nm LED (light emitting diode) at 37° C. for 15 minutes. After the reaction, 50 µL of a HEPES buffer solution containing a 0.1% horse serum-containing medium was added to thereto (final Aβ concentration: 10 µM). The mixture was incubated at 37° C. for 48 hours under 5% $CO_2$ atmosphere. A cell count reagent containing WST-8 (2-(2-methoxy-4-nitrophenyl)-3-(4-nitrophenyl)-5-(2,4-disulfonyl)-2H-tetrazolium, monosodium salt) (10 µL) was added to the mixture. The mixture was incubated at 37° C. for 6 hours under 5% $CO_2$ atmosphere. Thereafter, absorbance at 450 nm (reference wavelength: 655 nm) was measured by iMark™ plate reader (Bio-Rad Laboratories, Inc., Hercules, Calif.).

FIG. 17 shows the results. In order to achieve Aβ selective oxidation, a peptide having a high affinity for Aβ, D-[Lys-Leu-Val-Phe(4-phenyl)-Phe] (SEQ ID NO: 3) was identified, and was bonded to flavin as an affinity tag of Aβ (Catalyst 2 in FIG. 17). Catalyst 2 or riboflavin itself (Catalyst 1 in FIG. 17) was added to a phosphate buffer containing Aβ, and the mixture was irradiated with light in the presence of cells. 500 nm LED was used as a light source, and light was irradiated at 37° C. for 15 minutes. Here, as Catalyst 2 had oxidation activity lower than riboflavin itself, Catalyst 2 was used in an amount of five times that of riboflavin. It was confirmed that Catalysts 1 and 2 oxidized Aβ to a similar extent (about 60%) under the present conditions. After the oxidation reaction, the cells were further incubated for 2 days, and the cell viability was determined thereafter (bar graph in FIG. 17). When riboflavin was used under the light irradiation condition (comparison between f and h), almost all cells died regardless of the presence or absence of Aβ. It is conceivable that the cells were damaged due to non-specific oxidation. On the other hand, when Catalyst 2 was used in the absence of Aβ under the condition j, 50% or more of the cells survived after the light irradiation. It is conceivable that as Catalyst 2 itself has a relatively low oxidation activity, a random oxidation reaction of biomolecules may be inhibited. On the other hand, in the presence of Aβ (comparison between k and l), when the light was irradiated, the cell viability was significantly increased as compared with the case of no light irradiation. It is conceivable that Aβ was oxidized and detoxified, and thus the cell death was avoided. As described above, by using Catalyst 2, in the presence of the cells, the Aβ selective oxidation reaction successfully decreased the toxicity of Aβ.

The invention claimed is:

1. An oxidized Aβ peptide, comprising histidine 13 oxidized as a 14 Da adduct and histidine 14 oxidized as a 14 Da adduct.

2. A pharmaceutical composition comprising the oxidized Aβ peptide according to claim 1 and a pharmaceutically acceptable carrier.

3. The oxidized Aβ peptide according to claim 1, further comprising at least one of oxidized Histidine 6, oxidized Tyrosine 10, and oxidized Methionine 35.

4. A pharmaceutical composition comprising the oxidized Aβ peptide according to claim 3 and a pharmaceutically acceptable carrier.

5. The oxidized Aβ peptide according to claim 1, further comprising at least two of oxidized Histidine 6, oxidized Tyrosine 10, and oxidized Methionine 35.

6. A pharmaceutical composition comprising the oxidized Aβ peptide according to claim 5 and a pharmaceutically acceptable carrier.

7. The oxidized Aβ peptide according to claim 1, further comprising oxidized Histidine 6, oxidized Tyrosine 10, and oxidized Methionine 35.

8. A pharmaceutical composition comprising the oxidized Aβ peptide according to claim 7 and a pharmaceutically acceptable carrier.

* * * * *